US00PP14796P2

(12) United States Plant Patent
Danziger

(10) Patent No.: US PP14,796 P2
(45) Date of Patent: May 18, 2004

(54) GYPSOPHILA NAMED 'DANGYPURNA'

(50) Latin Name: *Gypsophila paniculata*
Varietal Denomination: Dangypurna

(75) Inventor: Gabriel Danziger, Nir-Zvi (IL)

(73) Assignee: Danziger "Dan" Flower Farm, Hashiva (IL)

( * ) Notice: Subject to any disclaimer, the term of this patent is extended or adjusted under 35 U.S.C. 154(b) by 0 days.

(21) Appl. No.: 10/339,345

(22) Filed: Jan. 10, 2003

(51) Int. Cl.[7] ..... A01H 5/00

(52) U.S. Cl. ..... Plt./354

(58) Field of Search ..... Plt./354

*Primary Examiner*—Kent Bell
(74) *Attorney, Agent, or Firm*—Foley & Lardner

(57) ABSTRACT

A new and distinct Gypsophila plant named 'Dangypurna' characterized by having white semi-double flowers (in winter) to double flowers (in summer), depending on growing conditions, globular shape, 8–10 mm corolla diameter; conic inflorescence form; 90–100 cm plant height, 50–60 cm plant width, erect, branching from plant base; suitable as a commercial product for cut flowers; and vigorous growth habit.

2 Drawing Sheets

Latin name of the genus and species of the plant claimed: *Gypsophila paniculata.*
Variety denomination: Dangypurna.

BACKGROUND OF THE INVENTION

The present invention relates to a new and distinct cultivar of Gypsophila plant, botanically known as *Gypsophila paniculata*, hereinafter referred to by the cultivar name 'Dangypurna'.

The new cultivar was derived from an open pollination with a proprietary female cultivar and unknown male parent made in a controlled breeding program in Mishmar Hashiva, Israel. The female parent is a proprietary unpatented cultivar from a hybrid line identified as '1102'. The male parent is open pollination. 'Dangypurna' was discovered and selected by the inventor, Gabriel Danziger, as a flowering plant within the progeny of the open pollination in a controlled environment in Mishmar Hashiva, Israel.

Asexual reproduction of the new cultivar by removing a cutting from the initial plant was first performed in December, 1999 in Mishmar Hashiva, Israel and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'Dangypurna' which in combination distinguish this Gypsophila as a new and distinct cultivar:

1. White semi-double flowers (in winter) to double flowers (in summer), depending on growing conditions; globular shape, 8–10 mm corolla diameter;
2. Conic inflorescence form;
3. 90–100 cm plant height, 50–60 cm plant width, erect, branching from plant base;
4. Suitable as a commercial product for cut flowers; and
5. Vigorous growth habit.

'Dangypurna' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown in Mishmar Hashiva, Israel under conditions which closely approximate those generally used in commercial practice.

Of the many commercial cultivars known to the present inventor, the most similar in comparison to 'Dangypurna' is the Gysophila cultivar 'Dangypflash' (U.S. Plant Pat. No. 12,422). In comparison to 'Dangypflash', 'Dangypurna' has a higher stem yield, more upright growth habit and more symmetrical flowers.

The following is a comparison chart between 'Dangypurna' and the female parental cultivar.

TABLE 1

| Characteristic | 'Dangypurna' | Female parental cultivar '1102' |
|---|---|---|
| Flower | Semi-double in winter, double in summer, 8–10 mm in diameter; white in color | Semi-double, 7–8 mm in diameter, white in color |
| Average stem weight during summer | 35–40 grams | 24–30 grams |
| Flowering rate in weeks during winter | 14–15 | 12–13 |
| Yield, stems per plant in first flash | 10–12 | 7–9 |

BRIEF DESCRIPTION OF THE DRAWING

The accompanying photographic drawings show typical flowers and foliage of a 12 week old 'Dangyppink' plant, with colors being as true as possible with illustrations of this type.

The first drawing is a view of a flowering stem of 'Dangypurna'.

The second drawing is a a close-up view of the flower and buds of 'Dangypurna'.

DETAILED BOTANICAL DESCRIPTION

The following observations, measurements and values describe the new cultivar at 12 weeks, as grown in Mishmar Hashiva, Israel under conditions which closely approximate those generally used in commercial practice. Regular cultural practices common for gypsophila in commercial fields were applied. Avoid excess GA or lighting. Color references are made to The Royal Horticultural Society Colour Chart (R.H.S.), except where general colors of ordinary significance are used. Color values were taken under daylight conditions at approximately noon in Mishmar Hashiva, Israel.

Propagation: Stem cutting.

Plant:

*General appearance and form.*—Height: 90–100 cm. Width: 50–60 cm. Habit: Weak apical dominance, branching from plant base. Form: Upright bush type. Flowering Response: Long day. Flowering Season: Naturally during summer; all year with suplemental lighting. Winter Hardiness: Temperature tolerant down to 0 C. Lastingness of the Individual Bloom: As a cut flower 6–8 days at room temperature; 4–5 days on the plant. Lastingness of the Inflorescence: As a cut flower 10–12 days at room temperature; 8–10 days on the plant. Fragrance: Typical of gypsophila.

Foliage:

*Amount.*—Scarce.

*Attachment.*—Sessile.

*Overall shape of leaf.*—Lanceolate. Base: Truncate. Tip: Acuminate.

*Margin.*—Entire.

*Texture.*—Rough.

*Main color of upper surface.*—Mature leaf: Green 137-A. Immature leaf: Green 137-A.

*Main color of lower surface.*—Mature leaf: Green 137-B. Immature leaf: Green 137-B.

*Venation.*—None.

*Size.*—Length: 6–7 cm. Width: 1–1.5 cm.

*Stipules.*—None.

Inflorescence:

*Natural flowering season.*—Long day.

*Corolla.*—Form: Semi-double (in winter) to double (in summer) depending on growing conditions. Shape: Globular. Average Number: 900–1000 flowers per flowering stem. Size: 8–10 mm diameter. Petal Number: 45–50. Petal Shape: Spatulate with truncate tip; margin: entire. Petal Size: 4 mm length; 1 mm width. Petal Markings: None. Petal Color: White RHS 155-D (both surfaces). Sepal Shape: Lanceolate; apex acuminate; margin entire. Sepal Size: 3 mm length; 1 mm width. Sepal Color: Green, RHS 143A.

*Stem.*—Growth habit: Upright and notably stable; the side stems are close to the main stem, forming inflorescence of several canopies, creating a wide and impressive structure; both flowers of the side stems and the main stem open almost simultaneously. Average length: 90–100 cm. Average diameter: 5–6 mm. Color: Yellow-Green 144-A. Internode length: 3–4 cm.

*Spur.*—None.

*Bud.*—Response: Long day. Color: Greenish white. Shape: Oblate. Size before opening: Length — 3 mm; width — 4 mm. Pedicel Length: 8–10 mm. Pedicel Color: Yellow-Green RHS 146-A.

*Reproductive organs.*—Stamen: 5–10 in number, however seldom seen; white in color. Seeds: Width: 1 mm. Length: 1 mm. Shape: Kidney shaped. Color: Black-Brown. Fruit: Color: Light Brown. Anthers: 5–10 in quantity, however seldom seen; white in color. Pollen: White in color. Stigma: 2 pistils convex; white in color. Ovary: Green in color.

Disease resistance: No susceptibility to disease was observed under regular growing condition.

I claim:

1. A new and distinct Gypsophila plant named 'Dangypurna', substantially as illustrated and described herein.

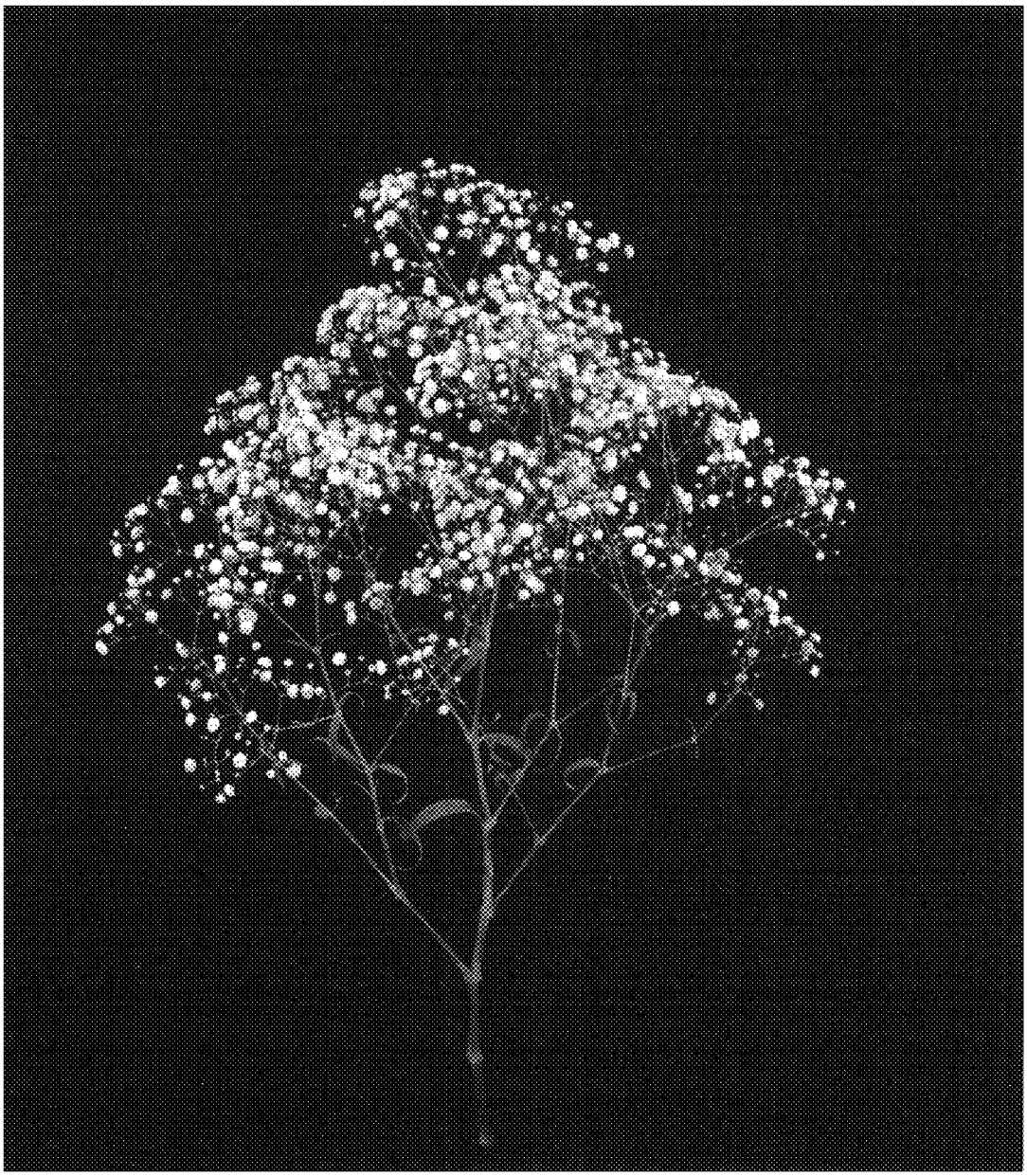

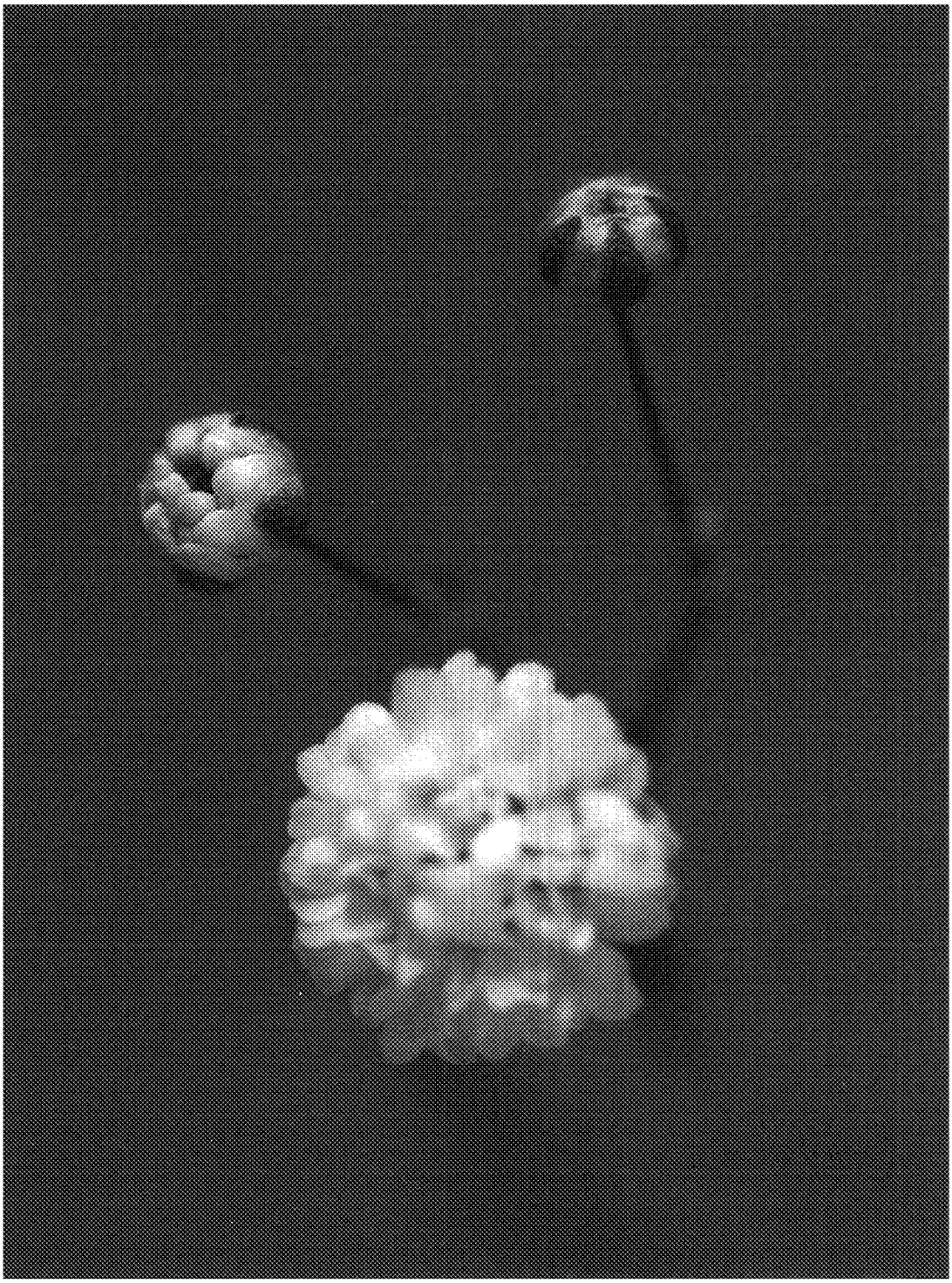

* * * * *